Figure 1:
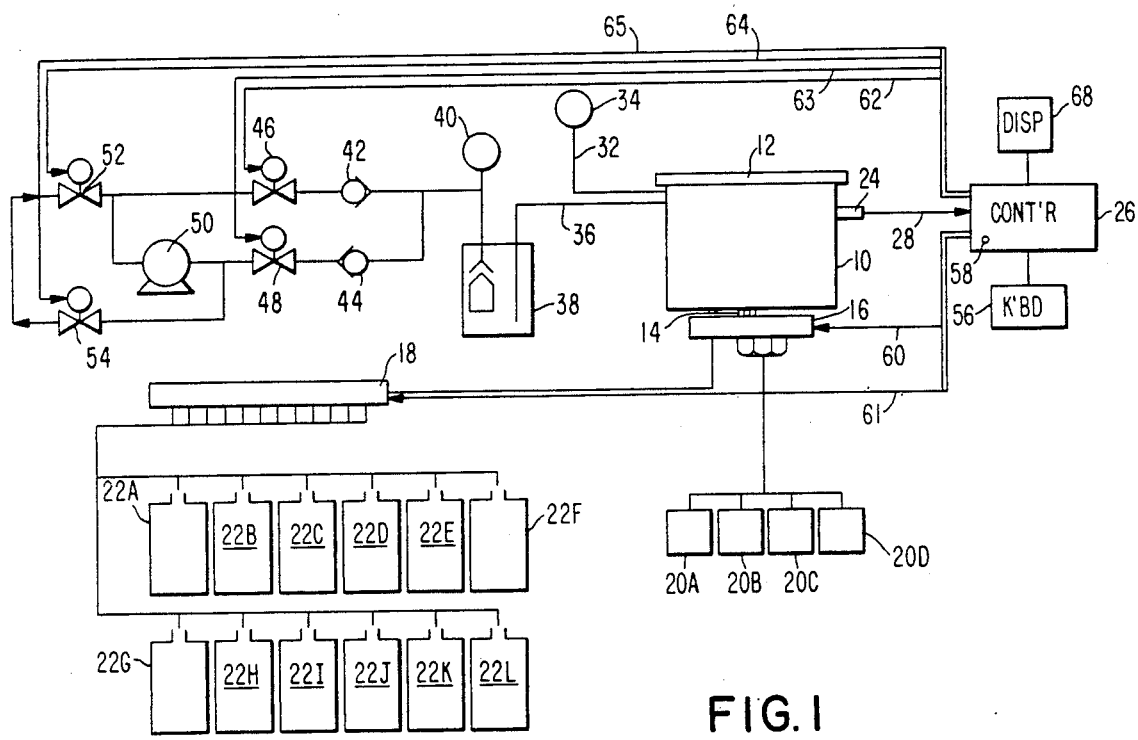

United States Patent [19]

Repasi et al.

[11] Patent Number: 5,049,510
[45] Date of Patent: Sep. 17, 1991

[54] PROCESS FOR HISTOLOGICAL TISSUE SPECIMEN TREATMENT THAT INCLUDES VARIABLE SENSITIVITY LEVEL CONTROL

[75] Inventors: Roger J. Repasi, Monroeville, Pa.; David G. Abichaker, West Roxbury, Mass.; Jerry C. Premus, Scottdale, Pa.

[73] Assignee: Fisher Scientific Company, Pittsburgh, Pa.

[21] Appl. No.: 461,379

[22] Filed: Jan. 5, 1990

[51] Int. Cl.$^5$ .......................... G01N 1/30; A01N 1/00; B05D 1/36
[52] U.S. Cl. .................... 436/176; 422/292; 435/291; 427/4; 118/429
[58] Field of Search ................ 436/176, 174; 422/1, 422/3, 110, 292; 435/3, 287, 291; 427/24; 118/429

[56] References Cited

U.S. PATENT DOCUMENTS

| | | | |
|---|---|---|---|
| 3,526,203 | 9/1970 | Kinney et al. | 118/429 |
| 3,892,197 | 7/1975 | Kinney et al. | 118/429 |
| 4,141,312 | 2/1979 | Louder et al. | |
| 4,358,470 | 11/1982 | Rasmussen | 118/429 |
| 4,363,783 | 12/1982 | Sitte | 422/63 |
| 4,399,433 | 8/1983 | Louder et al. | |
| 4,483,270 | 11/1984 | Toya et al. | 118/429 |
| 4,604,964 | 8/1986 | Gordon et al. | |
| 4,834,019 | 5/1989 | Gordon et al. | |

OTHER PUBLICATIONS

Fisher Scientific, Bulletin No. 661B, "MVP, MVPII" (Jan., 1987).

Primary Examiner—David L. Lacey
Assistant Examiner—Jan M. Ludlow
Attorney, Agent, or Firm—Fish & Richardson

[57] ABSTRACT

A histological tissue specimen treatment process includes the steps of placing a plurality of histological tissue specimens to be processed in chamber structure, closing the chamber structure, monitoring the level of a first tissue processing material flowed into the chamber structure with a sensor system that responds to a characteristic of the first tissue processing material, terminating the flow of the first tissue processing material when the histological tissue specimens are immersed in the first tissue processing material, flowing the first tissue processing material from the chamber structure after the histological tissue specimens have been immersed in the first tissue processing material for a predetermined time interval, monitoring the level of a second tissue processing material flowed into the chamber structure with the sensor system in a changed sensitivity condition, terminating the flow of the second tissue processing material when the plurality of histological tissue specimens are immersed in the second tissue processing material, and flowing the second tissue processing material from the chamber structure after the plurality of histological tissue specimens have been immersed in the second tissue processing material for a predetermined time interval.

8 Claims, 1 Drawing Sheet

PROCESS FOR HISTOLOGICAL TISSUE SPECIMEN TREATMENT THAT INCLUDES VARIABLE SENSITIVITY LEVEL CONTROL

This invention relates to processing systems and more particularly to methods and apparatus for processing histological tissue specimens.

Histological tissue specimens, preparatory to sectioning, mounting and staining for microscopic examination, are conventionally subjected to a processing sequence of fixing, dehydrating, clearing and embedding agents. In a typical tissue processing apparatus, tissue specimens are placed in a chamber that has a capacity of one hundred or more tissue cassettes, and the chamber is selectively connected to a series of reagent sources, each reagent being drawn into the chamber by vacuum and flowed from the chamber for return to a reagent container by gravity drain or by pressurizing the chamber. The specimens being processed can be quickly damaged or destroyed, at significant expense and inconvenience, by heat and/or exposure (dehydration) if they are not properly submerged in an appropriate processing reagent. A typical processing sequence is several hours in duration, and may be performed overnight or over a number of days, and accordingly it is desirable to monitor the liquid reagent material in the processing chamber. Suitable processing reagent materials include aqueous formaldehyde solutions for fixing, ethyl alcohol reagents of progressively increasing concentration for dehydration, xylene, a limonene-based solvent or similar material for clearing to displace the alcohol, and a material such as heated paraffin wax for embedding prior to sectioning. Such processing reagents have diverse characteristics and include aqueous solutions with relatively high dielectric constants and petroleum based materials with relatively low dielectric constants. For example, the dielectric constant of water is 78, dielectric constants of alcohols are in the range of 25 to 40; xylene has a dielectric constant in the range of 2.2–2.5, paraffin waxes have dielectric constants in the range of 1.1 to 2.5, and air has a dielectric constant of about 1. During a processing cycle, the temperature of the chamber could be as high as 65° C. for a heated embedding wax such as paraffin or as low as ambient temperature (e.g., 15° C.) for other processing liquids.

In accordance with one aspect of the invention, there is provided apparatus for processing histological tissue specimens that includes chamber structure for histological tissue specimens to be processed, conduit structure for connecting the chamber structure to a plurality of containers for tissue processing materials, pressure differential means for flowing processing materials from the containers into and out of the chamber structure; controller means for controlling the sequence of flow of processing materials into and out of the processing chamber; and a system for sensing the level of a processing material in the chamber structure, the sensing system including a sensor responsive to a characteristic of the processing materials and means for varying the sensitivity of the sensor; the controller means including means for varying the sensitivity of the sensor as a function of the selected processing material to be flowed into the chamber structure.

In a particular embodiment, the chamber structure is of metal, the processing materials include a fixing agent, a dehydrating agent, a clearing agent, and an embedding agent; the sensor is of the capacitive type; a polymeric isolation membrane structure isolates the sensor from the metal chamber structure, and the sensitivity varying means includes a resistive divider network, the effective resistance of which is changed as a function of the processing material selected for flow into the chamber structure.

In accordance with another aspect of the invention, there is provided a histological tissue specimen treatment process that includes the steps of placing a plurality of histological tissue specimens to be processed in chamber structure, sealing the chamber structure, flowing a first tissue processing material into the chamber structure under the influence of a pressure differential, monitoring the flow of the first tissue processing material into the chamber structure with a sensor system that responds to a characteristic of tissue processing material, terminating the flow of the first tissue processing material when the sensor indicates that the first tissue processing material has reached a predetermined level in the chamber structure such that the plurality of histological tissue specimens are immersed in the first tissue processing material, flowing the first tissue processing material from the chamber structure after the plurality of histological tissue specimens have been immersed in the first tissue processing material for a predetermined time interval, changing the sensitivity of the sensor system as a function of a characteristic of a second tissue processing material, flowing the second tissue processing material into the chamber structure under the influence of a pressure differential, monitoring the flow of the second tissue processing material into the chamber structure with the sensor system in the changed sensitivity condition, terminating the flow of the second tissue processing material when the sensor system indicates that the second tissue processing material has reached a predetermined level in the chamber structure such that the plurality of histological tissue specimens are immersed in the second tissue processing material, flowing the second tissue processing material from the chamber structure after the plurality of histological tissue specimens have been immersed in the second tissue processing material for a predetermined time interval, unsealing the chamber structure, and removing the plurality of processed histological tissue specimens from the chamber structure.

In particular processes, the sensor system monitors the flow of the tissue processing material into the chamber structure in a frequent, repetitive manner, for example, once every second; the processing materials include an aqueous solution with a relatively high dielectric constant and a petroleum based material with a relatively low dielectric constant; and the sensitivity of the sensor system is changed as a function of the dielectric constant of the processing material to be flowed into the chamber structure. In a particular process, the tissue processing materials include a fixing agent, a dehydrating agent, a clearing agent, and an embedding agent; the tissue processing materials are stored in separate containers and the sensitivity of the sensor system is changed as a function of a preprogrammed correlation between the container of a selected processing material to be flowed into the chamber structure and a characteristic of the selected processing material; the chamber structure is of metal and has a sensing port, and polymeric isolation membrane structure is sealingly disposed across the sensing port for isolating the sensor system from the metal chamber structure; and the sensor system is of the capacitive type and includes a sensing face seated on the polymeric isolation membrane structure.

Figure 2:
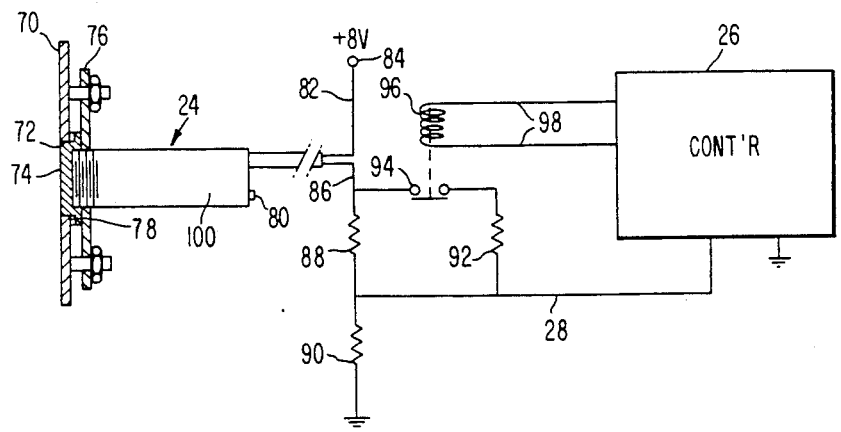

Other features and advantages of the invention will be seen as the following description of a particular embodiment progresses, in conjunction with the drawings, in which:

FIG. 1 is a block diagram of a tissue processing system in accordance with the invention; and FIG. 2 is a schematic diagram of the level sensor and sensitivity control employed in the system shown in FIG. 1.

Description of Particular Embodiment

With reference to FIG. 1, the tissue processing system includes stainless steel process chamber 10 with sealable cover 12. Conduit 14 extends from the bottom of chamber 10 through selector valve 16 which is connected to selector valve 18 and to a series of four (two liter volume) paraffin reservoirs 20A-D. Rotary select valve 18 is adapted to selectively connect one of twelve (two liter) containers 22 for processing materials through selector valve 16 to processing chamber 10—two containers 22A and 22B of 10% Formalin (4% formaldehyde in water, with or without a buffer, such as sodium phosphate); two containers 22C and 22D of 70% ethanol; two containers 22E and 22F of 95% ethanol; three containers 22G-22I of 100% ethanol; and three containers 22J-22L of xylene.

Mounted on the wall of process chamber 10 is level sensor 24 that is connected to controller 26 by line 28. Also coupled to process chamber 10 by line 32 is pressure transducer 34, and by exhaust conduit 36 is trap bottle 38. Trap bottle 38 is connected to overflow vacuum switch 40 and through check valves 42, 44 and control valves 46, 48 to vacuum pump 50. Solenoid valve 52 connects pump 50 to a vent and solenoid valve 54 connects pump 50 to a charcoal filter. Controller 26 has inputs from keyboard 56 and from level sensor 24, responds to processor start button 58, and provides control outputs over lines 60-65 to valves 16, 18, 46, 48, 52 and 54, and an output to display 68.

With reference to FIG. 2, the stainless steel wall 70 of process chamber 10 has port 72 against which a one inch diameter and 0.15 inch thick Tefzel (a TFE fluoropolymer) dielectric membrane window 74 is secured by clamp plate 76 and sealed with O-ring 78.

Level sensor 24 is a capacitive sensor (Turck Model BC10-S18-YOX) that has sensitivity adjustment 80 and output lines 82 (connected to a plus eight volt source at terminal 84) and 86 (connected to a divider network of series resistors 88 and 90. Resistor 92 is connected in series circuit with contacts 94 that are controlled by relay 96 in response to signals from controller 26 over lines 98. The divider network has a resistance of about two kilohms when relay contacts 94 are open and a resistance of about 890 ohms when relay contacts 94 are closed. Capacitive level sensor 24 includes an RC oscillator with a sensing electrode mounted in a conductive tube 100 that is threadedly mounted on clamp plate 76 so that its sensing face is seated on Tefzel window 74.

The current output of the level sensor circuitry is applied over line 28 to a twelve-bit analog digital converter in controller 26. When the system is to sense a high dielectric material (water or alcohol), controller 26 deenergizes relay 96 so that its contacts 94 are open. When a low dielectric material is in chamber 10, controller 26 energizes relay 96 to close relay contacts 94.

The operator programs the sequence of processing materials and time duration of each processing material in controller 26 using keyboard 56. The programmed sequence may be displayed for operator reference on display 68. A typical operational sequence of the system is set out in the table below:

| Station | Time (min.) | Reagent | Temp (°C.) |
| --- | --- | --- | --- |
| 22A | 60 | 10% Formalin | 15 |
| 22B | 120 | 10% Formalin | 15 |
| 22C | 45 | 70% Ethanol | 15 |
| 22E | 45 | 95% Ethanol | 15 |
| 22F | 45 | 95% Ethanol | 15 |
| 22G | 45 | 100% Ethanol | 15 |
| 22H | 45 | 100% Ethanol | 15 |
| 22I | 45 | 100% Ethanol | 15 |
| 22J | 45 | Xylene | 15 |
| 22K | 45 | Xylene | 15 |
| 20A | 45 | Tissue Prep II | 60 |
| 20B | 45 | Tissue Prep II | 60 |
| 20C | 45 | Tissue Prep II | 60 |

In system operation, a load of tissue cartridges is placed in processing chamber 10 and cover 12 is sealed. Start button 58 is actuated and the processor controller 26 commences a processing sequence. Each processing material is drawn into process chamber 10 by vacuum generated by pump 50 through overflow bottle 38 and valve 46. At the beginning of each fill interval, level sensor 24 is set to the appropriate sensitivity level of the processing material as determined by a preprogrammed correlation the container 20 A-D or 22 A-L and a position for relay 96. The Formalin and alcohol materials have high dielectric constants, and therefore relay 96 opens contacts 94. A reference value from sensor 24 is stored in controller 26 and the filling sequence is commenced by opening of valve 46. Controller 26 senses the output of sensor 24 once every second, and compares that sensed valve with the stored reference value. When two consecutive outputs from level sensor on line 28 are determined by controller 26 to exceed a predetermined offset from the stored reference value, controller 26 terminates the fill sequence by closing valve 46. The tissue specimens are immersed in the Formalin material for the programmed duration (one hour in the above illustrative processing sequence). At the end of that programmed time interval, vent valve 52 is opened and the processing liquid is returned to its supply container 22A through selector valves 16 and 18 by gravity.

The chamber fill and treatment sequences are repeated, according to the programmed schedule for successive immersions in different alcohols for dehydrating, clearing by immersion in xylene; and embedding by immersion of the tissue specimens in heated paraffin wax. When a low dielectric constant material (xylene or paraffin wax) is selected (as determined by station 22J, 22K, or 20 A-D being connected), the controller 26 energizes relay 96 to close contacts 94 and connect resistor 92 in parallel with resistor 88, changing the sensitivity of the sensor circuitry by reducing the effective resistance of the current source divider network.

While a particular embodiment of the invention has been shown and described, various modifications thereof will be apparent to those skilled in the art, and therefore it is not intended that the invention be limited to the disclosed embodiment, or to details thereof, and departures may be made therefrom within the spirit and scope of the invention.

What is claimed is:

1. A histological tissue specimen treatment process comprising the steps of placing a plurality of histological tissue specimens to be processed in an open chamber structure, closing said open chamber structure, flowing a first tissue processing material into said chamber structure under the influence of a pressure differential, monitoring the level of said first tissue processing material in said chamber structure with a sensor system that responds to a characteristic of the tissue processing material, terminating said flow of said first tissue processing material when said sensor system indicates that said first tissue processing material has reached a predetermined level in said chamber structure such that said plurality of histological tissue specimens are immersed in said first tissue processing material, flowing said first tissue processing material from said chamber structure after said plurality of histological tissue specimens have been immersed in said first tissue processing material for a predetermined time interval, changing the sensitivity of said sensor system as a function of a characteristic of a second tissue processing material, flowing said second tissue processing material into said chamber structure under the influence of a pressure differential, monitoring the level of said second tissue processing material in said chamber structure with said sensor system in said changed sensitivity condition, terminating said flow of said second tissue processing material when said sensor system indicates that said second tissue processing material has reached a predetermined level in said chamber structure such that said plurality of histological tissue specimens are immersed in said second tissue processing material, flowing said second tissue processing material from said chamber structure after said plurality of histological tissue specimens have been immersed in said second tissue processing material for a predetermined time interval, opening said chamber structure, and removing said plurality of processed histological tissue specimens from said chamber structure.

2. The process of claim 1 wherein said sensor system monitors the level of said tissue processing material in said chamber structure in a frequent, respective manner.

3. The process of claim 2 wherein said chamber structure is made of metal, and further including polymeric isolation membrane structure positioned and arranged so as to isolate said sensor system from said metal chamber structure.

4. The process of claim 1 wherein said first processing material includes an aqueous solution with a relatively high dielectric constant and said second processing material includes a petroleum-based material with a relatively low dielectric constant, and the sensitivity of said sensor system is changed as a function of the dielectric constant of the processing material to be flowed into said chamber structure.

5. The process of claim 1 wherein said first and second tissue processing materials are stored in separate containers and the sensitivity of said sensor system is changed as a function of a preprogramed correlation between the container of a selected one of the processing materials to be flowed into said chamber structure and a characteristic of the selected processing material.

6. The process of claim 5 wherein said chamber structure is made of metal and has a sensing port, and further including polymeric isolation membrane structure sealingly disposed across said sensing port for isolating said sensor system from said metal chamber structure, and said sensor system is of the capacitive type and includes an RC oscillator with a sensing face mounted on said chamber structure so that said sensing face is seated on said polymeric isolation membrane structure.

7. The process of claim 1 wherein said first processing material is selected from the group consisting of fixing agent and a dehydrating agent, said second processing material is selected from the group consisting of a clearing agent, and an embedding agent, the level of said first processing material in said chamber structure is monitored with said sensor system in a first sensitivity condition, and the level of said second processing material in said chamber structure is monitored with said sensor system in a second sensitivity condition different from said first sensitivity condition.

8. The process of claim 7 wherein said chamber structure is made of metal and has a sensing port, and further including polymeric isolation membrane structure sealingly disposed across said sensing port for isolating said sensor system from said metal chamber structure, said sensor system is of the capacitive type and includes an RC oscillator and a sensing face mounted on said chamber structure so that said sensing face is seated on said polymeric isolation membrane structure, said first and second tissue processing materials are stored in separate containers, and the sensitivity of said sensor system is changed as a function of a preprogrammed correlation between the selected container of a one of the processing materials to be flowed into said chamber structure and a dielectric characteristic of the processing material stored in said selected container.

* * * * *